United States Patent [19]

Kusserow

[11] 4,236,111

[45] Nov. 25, 1980

[54] METHOD AND APPARATUS FOR THE MEASUREMENT OF ELECTRIC CURRENTS AND/OR VOLTAGES IN A PLURALITY OF CURRENT OR VOLTAGE CIRCUITS

[75] Inventor: Bernd Kusserow, Erlangen, Fed. Rep. of Germany

[73] Assignee: Siemens Aktiengesellschaft, Berlin & Munich, Fed. Rep. of Germany

[21] Appl. No.: 11,042

[22] Filed: Feb. 9, 1979

[30] Foreign Application Priority Data

Mar. 8, 1978 [DE] Fed. Rep. of Germany ........ 2810046

[51] Int. Cl.³ .................... G01R 19/00; G01R 19/16
[52] U.S. Cl. ................................. 324/103 P
[58] Field of Search ............... 324/103 P, 115, 119, 324/123 R, 140 R

[56] References Cited

U.S. PATENT DOCUMENTS

| | | | |
|---|---|---|---|
| 3,775,675 | 11/1973 | Freeze et al. | 324/103 P X |
| 3,846,692 | 11/1974 | Hill | 324/103 P X |
| 3,903,470 | 9/1975 | Mirabile et al. | 324/103 P X |
| 4,023,574 | 5/1977 | Nemec | 128/420 A |
| 4,074,149 | 2/1978 | Naaijer | 324/103 P X |
| 4,166,245 | 8/1979 | Roberts | 324/103 P |

FOREIGN PATENT DOCUMENTS

| | | | |
|---|---|---|---|
| 2332268 | 1/1975 | Fed. Rep. of Germany | 324/103 P |
| 1435774 | 5/1976 | United Kingdom | 324/103 P |

Primary Examiner—Stanley T. Krawczewicz
Attorney, Agent, or Firm—Hill, Van Santen, Steadman, Chiara & Simpson

[57] ABSTRACT

Here, a means is to be created with which quick alterations in the signal behavior are grasped and displayed. Even with the use of peak value meters with very large time constants, such quick alterations are also to be used for the quick correction of the peak value display. In an exemplary embodiment, each separately registered current or voltage value from an individual current or, respectively, voltage circuit is compared at a comparator specifically allocated to it with a mean value which is formed from the current or, respectively, voltage values of all participating current or, respectively, voltage circuits. Upon nonequality of the current or, respectively, voltage values with the mean value within a predeterminable limit, the output signals of the comparators are then brought to display at a separately allocated display element. The invention is used particularly for the measurement of the peak value of middle frequency currents in middle frequency current circuits in electromedical interference current therapy.

12 Claims, 1 Drawing Figure

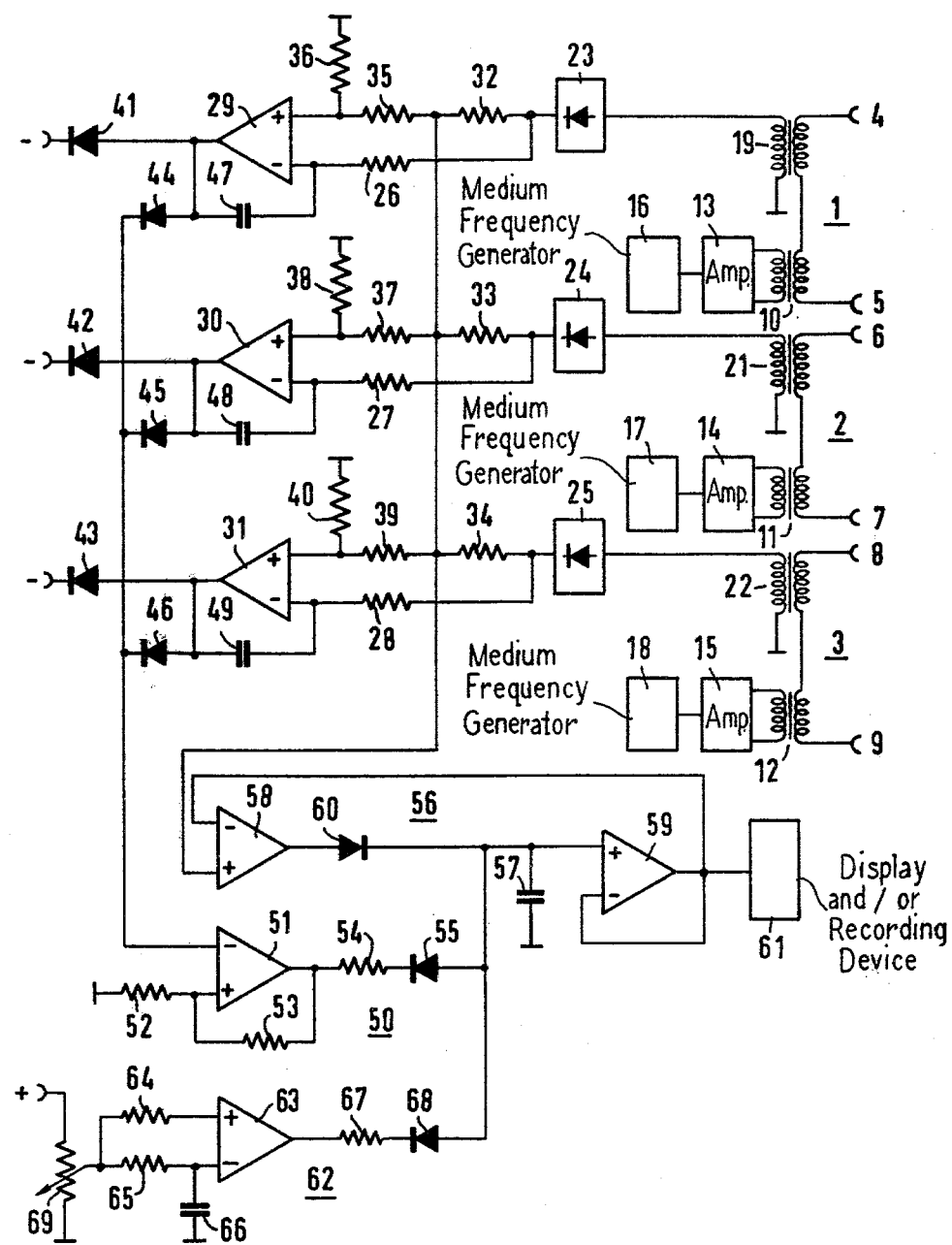

METHOD AND APPARATUS FOR THE MEASUREMENT OF ELECTRIC CURRENTS AND/OR VOLTAGES IN A PLURALITY OF CURRENT OR VOLTAGE CIRCUITS

BACKGROUND OF THE INVENTION

The invention relates to a method and apparatus for the measurement of electric currents and/or voltages in a plurality of current or, respectively, voltage circuits, particularly of the middle frequency current circuits in electromedical interference current therapy, whereby the current or voltage of each circuit is compared with a comparative value.

Current or voltage measurements are relatively unproblematic as long as the peak values are not subject to amplitude fluctuations that are all too slow. If, however, such slow amplitude fluctuations occur, then peak value meters with correspondingly large time constants must be employed so that the amplitude fluctuations do not influence the measurement of peak values. Thereby, the required time constant can be so large that changes in the signal behavior which result particularly from technical errors such as the falling off of electrodes ect. are not registered by the peak value meter. This would have as a result that a large peak value would continue to be indicated although, in the meantime, the current had sunk to a fraction of this peak value or entirely down to zero. In this sense, the same is also true for intentional intensity alterations; if the intensity value were regulated down to a lower value by means of an intensity regulator, then, in this case, too, the peak value display would remain unchanged. An area where these problems are particularly relevant is electromedical interference current therapy. Here, where one is always operating with a plurality of current or, respectively, voltage circuits (for example stereodynamic method according to U.S. Pat. No. 4,023,574), the display of the respective peak value of each circuit is always necessary. For the peak value meter used, however, the time constant must then be very large (at least in the minute range), so that, with a parallel arrangement of the circuits, the amplitude fluctuations of very low frequency (circa 0.01/s) which occur do not falsify the display result. However, in a peak value meter with such large time constants, the disadvantages described will then certainly always occur. A change of the transition resistance electrode to the skin or the complete falling off of an electrode will, therefore, not be displayed. A change of the intensity by means of intensity regulators can also not be controlled.

SUMMARY OF THE INVENTION

The object of the present invention is to create a means with which the quick alterations in the signal behavior can be registered and displayed or, respectively, also be used for the quick correction of the peak value display.

In a method of the type initially cited, the object is inventively achieved in that each separately registered current or voltage value is compared in a comparator specifically allocated to it with a mean value which is formed out of the current or, respectively, voltage values of all concerned current or, respectively, voltage circuits; and in that the output signals of the comparators upon non-equality of the current or, respectively, voltage values with the mean value within a predeterminable limit are delivered for display at a separately allocated display means.

If all of the currents or, respectively, voltages measured in such a method are equally large or deviate from one another other insignificantly within a predeterminable limit, then all of the comparators are in the same switching state. If, on the other hand, the current or, respectively, voltage of at least one of the circuits deviates from the current or, respectively, voltage values of the other circuits and transgresses the predetermined limit for the deviation, then the corresponding comparator switches over into the other switching state. The deviant behavior of the current or, respectively, voltage circuit is indicated by means of the response of the appertaining indicator.

In an advantageous embodiment of the invention, a display should at least then always ensue when the current or, respectively, voltage value measured falls below the mean value of the currents or, respectively, voltages of all circuits by a rate per hundred which lies at about 10 to 20%. This ensues most expediently at the comparator in that the mean value at the mean value input is lowered by means of voltage division by the desired rate per hundred in contrast to the actual value.

With the display of the altered current or, respectively, voltage relationships in a current or, respectively, voltage circuit, a correction of the peak value display is also to be simultaneously undertaken. To this end, all outputs of the comparators are connected to a discharge circuit for the storage element of the peak value meter for its discharge upon an altered mean value. Further, it is to be recommended that a discharge circuit be also provided for discharging the storage element of the peak value meter as a function of intensity alterations at an intensity regulator. In this case, thus, upon each intentional intensity change, the peak value of a peak value meter with a very large time constant per se is quickly adapted to the actual value.

Further advantages and details of the invention derive from the following description of an exemplary embodiment of the invention in conjunction with the further subclaims; and other objects, features and advantages will be apparent from this detailed disclosure and from the appended claims.

BRIEF DESCRIPTION OF THE DRAWING

The single FIGURE comprises an electric circuit diagram for illustrating an exemplary embodiment in accordance with the present invention.

DETAILED DESCRIPTION

In the FIGURE, which shows a sample embodiment in basic circuit diagram, reference numerals 1, 2 and 3 designate current circuits for interference current therapy. The terminals 4 through 9 indicate the connections for the pairs of required stimulating current electrodes. The supply of the individual circuits 1, 2 or 3, respectively, ensues by means of transformer coupling at 10, 11 or 12, respectively, via pushpull amplifier stages 13, 14, 15 as a function of medium frequency generators 16, 17, 18. The currents to be fed in lie in the middle frequency range between 1,000 and 100,000 Hz.

The input of the current or, respectively, voltage values at the individual current circuits 1, 2, 3 ensues via a further inductive coupling 19, 21, or 22, respectively. The current or, respectively, voltage values obtained in that manner are rectified in rectification circuits 23, 24, 25. After rectification, there ensues the delivery to operational amplifiers 29, 30, 31, which serve as comparators for the comparison with a mean value. Thereby, the rectified current or, respectively, voltage values are directly supplied to the inverting inputs of each operational amplifier 29, 30, or 31, respectively, via a resistor 26, 27 or 28, respectively. However, the signals are also simultaneously conducted by means of parallel connection to the mean value via the resistors 32, 33 and 34. The mean value signal is then supplied via the voltage dividers, 35, 36 or 37, 38 or 39, 40 to the noninverting inputs of the operational amplifiers 29, 30 or 31, respectively. The dimensioning of the individual voltage dividers is selected in such manner that, by means of them, the respectively appearing mean value of the current or, respectively, voltage values of all concerned circuits 1, 2, 3 is lowered at the non-inverting input of each operational amplifier 29 through 31 by about 10 through 20% in comparison to the actual value. In the comparison of the signal value of the current or, respectively, of the voltage with the mean value, thus, an output signal (e.g. a logical one or "high" value) is yielded at the output of each operational amplifier 29, 30 or 31 when the current or, respectively, voltage value of one of the circuits falls below the measured mean value of all participating circuits by the selected limit between 10 through 20%. The signal thereby occurring at the output of the operational amplifier 29, 30 or 31 is brought to display at the output of such operational amplifier by means of light-emitting diode 41, 42 or 43, respectively.

Simultaneously, the peak current value of a peak value meter is also corrected downward via a discharge installation connected on the output side via diodes 44 through 46. A flickering of the luminous display of the light-emitting diodes 41, 42 or 43 upon a brief current decline is prevented by means of integration capacitors 47, 48 or 49, respectively. The discharge installation is designated with 50. It comprises an operational amplifier 51 along with the wiring resistors 52, 53, 54 and discharge diode 55. The peak value meter 56 comprises the storage capacitor 57 to be discharged. This is connected on its input side via an operational amplifier 58 with diode 60 to the mean value input of each of the operational amplifiers 29, 30 and 31. Diode 55 is the coupling element for the coupling to the discharge circuit 50. The display of the respective peak value ensues at the display or, respectively, recording device 61 via the operational amplifier 59.

A discharge of the charge storage 57 in the peak value meter 56 also ensues when the intensity of the currents to be supplied is intentionally altered. A suitable discharge circuit again comprises an operational amplifier 63 with circuit resistors 64, 65 and 67 and discharge diode 68. Further, the inverting input of the operational amplifier 63 has a delay capacitance 66 connected therewith. Both inputs of operational amplifier 63 are connected in common to the intensity regulator 69. When, therefore, the patient current is reduced by means of turning back the intensity regulator, then the peak value display is also automatically adapted to the reduced value. Thereby, the delay capacitance 66 in interplay with the resistor 65 effects that intensity increases by turning up the regulator 69 do not influence the signal behavior of the operational amplifier 63 at the output; the output of the operational amplifier remains at positive potential. Only a down-regulation of the intensity effects a changeover of the output to negative potential during the regulation time span and, thus, peak value discharge in the desired manner.

It will be apparent that many modifications and variations may be effected without departing from the scope of the novel concepts and teachings of the present invention.

I claim as my invention:

1. A method for the measurement of electric currents and/or voltages in a plurality of current or, respectively, voltage circuits, in particular of middle frequency current circuits in electromedical interference current therapy, whereby the current or voltage of each circuit is compared with a comparative value, characterized in that each separately registered current or voltage value is compared at a comparator (29, 30, 31) specifically allocated to it with a mean value which is formed from the current or, respectively, voltage values of all participating current or, respectively, voltage circuits (1, 2, 3); and in that the output signals of the comparators upon non-equality of a current or, respectively, voltage value with the mean value within a predeterminable limit are brought to display at a separately allocated display means (41 through 43).

2. A method according to claim 1, characterized in that the current or, respectively, voltage values of each circuit (1, 2, 3) are supplied to the one input of an operational amplifier (29, 30, 31) allocated to this circuit as a comparator, whereas the other input of the respective operational amplifier is supplied with the mean value of the currents or, respectively, voltages of all participating circuits (1 through 3) reduced by a predeterminable amount.

3. A method according to claim 2, characterized in that the reduction of the mean value ensues by means of voltage division to the end that the mean value is lowered by a certain rate per hundred with respect to the actual value.

4. A method according to claim 3, characterized in that the rate per hundred of the decrease lies in the range from about 10 through about 20%.

5. Apparatus for the implementation of the method according to claim 1, characterized by comparators (29, 30, 31) separately allocated to the current or voltage circuits (1, 2, 3) for comparison of the separately registered current or voltage values with a mean value of the current or, respectively, voltage values of all participating current or, respectively, voltage circuits and by indicators (41, 42, 43) at the output of the comparators.

6. Apparatus according to claim 5, characterized by an interconnection of said operational amplifiers (29, 30, 31) as comparators with the outputs of the current or, respectively, voltage circuits (1, 2, 3) in such manner that each circuit output on the one hand is separately connected with the input and on the other hand also with the other input of the appropriate operational amplifier via a common mean value former (32, 33, 34).

7. Apparatus according to claim 6, characterized in that, for the mean value formation, the outputs of all participating circuits (1 through 3) are connected in parallel via resistors (32 through 34).

8. Apparatus according to claim 5, characterized by a voltage divider (35, 36; 37, 38; 39, 40) at each mean value input of the operational amplifiers (29, 30, 31), which voltage divider divides the mean value voltage preferably in the ratio 1/10 through 1/5.

9. Apparatus according to claim 5, characterized in that, for the mean value formation, outputs of the individual current or, respectively, voltage circuits which are connected in parallel are also additionally connected with a peak value meter (56).

10. Apparatus according to claim 9, characterized in that the outputs of the comparators (29, 30, 31) are connected with a discharge circuit (50) for the storage element (57) of the peak value meter (56) for its discharge upon an altered mean value.

11. Apparatus according to claim 5, characterized in that a further discharge circuit (62) for the discharge of the storage element (57) of the peak value meter (56) is present and depends on intensity changes at an intensity regulator (69).

12. Apparatus according to claim 11, characterized in that the discharge circuit (62) comprises an operational amplifier (63) which is connected on its output side with the storage element (57) of the peak value meter (56) via a discharge diode (68) and is connected on its input side with the intensity regulator (69) via at least one RC-network (65, 66) at the input in accord with the polarity direction of the discharge diode (68).

* * * * *